United States Patent [19]

DeGroot

[11] Patent Number: 5,360,435
[45] Date of Patent: Nov. 1, 1994

[54] MULTIPLE PULSE CARDIOVERSION OR DEFIBRILLATION

[75] Inventor: Paul DeGroot, Brooklyn Park, Minn.

[73] Assignee: Medtronic, Inc., Minneapolis, Minn.

[21] Appl. No.: 19,509

[22] Filed: Feb. 19, 1993

[51] Int. Cl.⁵ .............................................. A61N 1/00
[52] U.S. Cl. .................................................. 607/7
[58] Field of Search ................................ 607/5.7, 6.8

[56] References Cited

U.S. PATENT DOCUMENTS

| 3,605,754 | 9/1971 | Jaros . | |
|---|---|---|---|
| 4,548,209 | 10/1985 | Wielders . | |
| 4,708,145 | 11/1987 | Tacker . | |
| 4,727,877 | 3/1988 | Kallok . | |
| 4,800,883 | 1/1989 | Winstrom . | |
| 4,830,006 | 5/1989 | Haluska . | |
| 4,850,357 | 7/1989 | Bach, Jr. . | |
| 4,953,551 | 9/1990 | Mehra . | |
| 4,971,058 | 11/1990 | Pless . | |
| 5,063,928 | 11/1991 | Grevis . | |
| 5,163,427 | 11/1992 | Keimel . | |
| 5,199,429 | 4/1993 | Kroll et al. | 128/419 |

FOREIGN PATENT DOCUMENTS 0280526  8/1988  European Pat. Off. ............... 607/5

Primary Examiner—Lee S. Cohen
Assistant Examiner—Marianne H. Parker
Attorney, Agent, or Firm—Reed A. Duthler; Harold R. Patton

[57] ABSTRACT

A cardioverter or defibrillator employing multiple electrode pairs. The device includes an output stage comprising two capacitors or capacitor banks which are connected in parallel during the discharge of the first pulse between the electrodes in one pair and are thereafter connected in series and discharged between the electrodes in a second electrode pair.

9 Claims, 3 Drawing Sheets

MULTIPLE PULSE CARDIOVERSION OR DEFIBRILLATION

BACKGROUND OF THE INVENTION

This invention relates generally to the field of electrical stimulators, and more particularly to cardioverters and defibrillators.

The earliest cardioverters and defibrillators generated either a single burst of alternating current or a single pulse for application to the heart to cause cardioversion or defibrillation. However, the use of multiple pulses to accomplish cardioversion or defibrillation has also been extensively researched. For example, U.S. Pat. No. 3,605,754 issued to Jaros, et al., on Sep. 20, 1971 discloses an early double pulse heart defibrillator employing two capacitors which are successively discharged between a single pair of electrodes. Later, the use of multiple electrode systems, in which defibrillation pulses were delivered successively between different electrode pairs chosen from among the electrodes available was suggested. For example, U.S. Pat. No. 4,727,877 issued to Kallok on Mar. 1, 1988 and U.S. Pat. No. 4,708,145 issued to Tacker, Jr. et al., on Nov. 24, 1987, both disclose a variety of implantable, multiple electrode systems adapted for use in conjunction with a sequential pulse defibrillator, in which pulses are applied sequentially to different pairs of electrodes.

The ability to deliver sequential pulses to different pairs of electrodes is incorporated in the Medtronic implantable pacemaker/cardioverter/defibrillators presently in clinical evaluation in the United States. The pulse generation circuitry in these devices corresponds generally to that disclosed in allowed U.S. Pat. No. 5,167,427, issued to Keimel, incorporated herein by reference in its entirety. In these devices, two capacitor banks are provided which are simultaneously charged and then successively or simultaneously discharged between different pairs of electrodes.

It has also been proposed to apply biphasic pulses to individual or multiple electrode pairs, in which a first pulse is followed by a second pulse of opposite polarity. The second pulse typically has an initial amplitude equal to the trailing edge amplitude of the first pulse, but at a reversed polarity, but may have an initial amplitude greater than or equal to the initial amplitude of the first pulse. Apparatus for delivering such biphasic pulses are disclosed in U.S. Pat. No. 4,850,357 issued to Bach, Jr. on Jul. 25, 1989, U.S. Pat. No. 4,953,551 issued to Mehra et al., on Sep. 4, 1990, and in U.S. Pat. No. 4,800,883 issued Jan. 31, 1989 to Winstrom, all of which are incorporated herein by reference in their entireties.

Some of the electrode configurations and pulse regimens described in the above-cited patents have all been tested clinically, and in at least some patients, provide a benefit as compared to a monophasic pulse regimen delivered between a single pair of electrodes. Some researchers have found that the use of a biphasic pulse regimen provides a reduction in the energy required to defibrillate, when the biphasic pulse is used in either a two electrode system or a three electrode system as proposed in Mehra, with two electrodes tied together during delivery of the biphasic pulse. Some researchers have also found that sequential delivery of monophasic pulses between two different electrode pairs, as described in the above-cited Kallok and Tacker Jr., references provides a reduction in energy thresholds as compared to sequentially delivered monophasic pulses.

Nonetheless, there is still a substantial desire for further reductions in overall energy thresholds associated with defibrillation, in the context of implantable defibrillators. Reduction of energy threshold allows for the use of smaller batteries or provides for increased longevity in these devices, and is an area of ongoing research activities, both within the medical community and by manufacturers of implantable cardioverters and defibrillators.

SUMMARY OF THE INVENTION

The present invention is directed at providing an incremental reduction in energy threshold in systems employing multiple pulses delivered sequentially between different electrode pairs. Rather than delivering sequential pulses of equal amplitude, successively, between different electrode pairs, using separate capacitor banks, the present invention sequentially delivers pulses between differing electrode pairs, by first discharging two capacitors or capacitor banks, in parallel, between a first pair of electrodes and thereafter discharges the two capacitors or capacitor banks, connected in series, between a second pair of electrodes. In this case, the amplitude of the second delivered pulse will be equal to twice the trailing edge amplitude of the first delivered pulse. By controlling the width of the first pulse as a function of tilt, the amplitude of the second pulse may be correspondingly controlled.

DETAILED DESCRIPTION OF THE PREFERRED EMBODIMENTS

Figure 1:
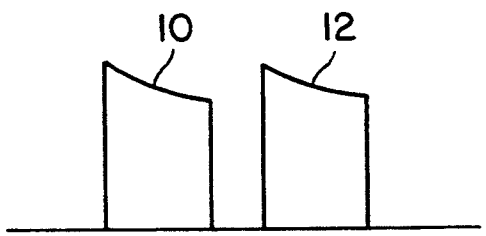
FIG. 1 is an illustration of sequentially applied defibrillation pulses.

FIG. 1 illustrates the delivered pulses of a prior art sequential pulse defibrillation system. As illustrated, the wave form comprises two successive truncated exponential, capacitive discharge wave forms 10 and 12. As described in the above-cited Jaros, et al., patent, these pulses are generally delivered using separate capacitor banks which are simultaneously charged and successively discharged. As described in the above-cited Tacker, et al., and Kallok, patents, in the context of multiple pulse, multiple electrode systems, the first pulse 10 is typically delivered between a first electrode pair and the second pulse 12 is typically delivered between a second electrode pair. The first and second electrode pairs may or may not have an electrode in common.

Figure 2:
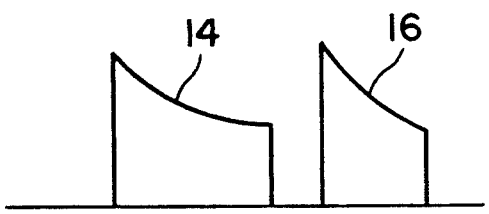
FIG. 2 is an illustration of sequentially applied defibrillation pulses according to the present invention.

FIG. 2 is an illustration of the multiple pulse output of the present invention. As illustrated, a first pulse 14 is delivered by discharging both capacitor banks in parallel and the second pulse 16 is delivered by continuing to discharge the capacitor banks, but connected in series. The first pulse 14 is delivered to a first pair of electrodes and the second pulse 16 is delivered to a second pair of electrodes.

Figure 3:
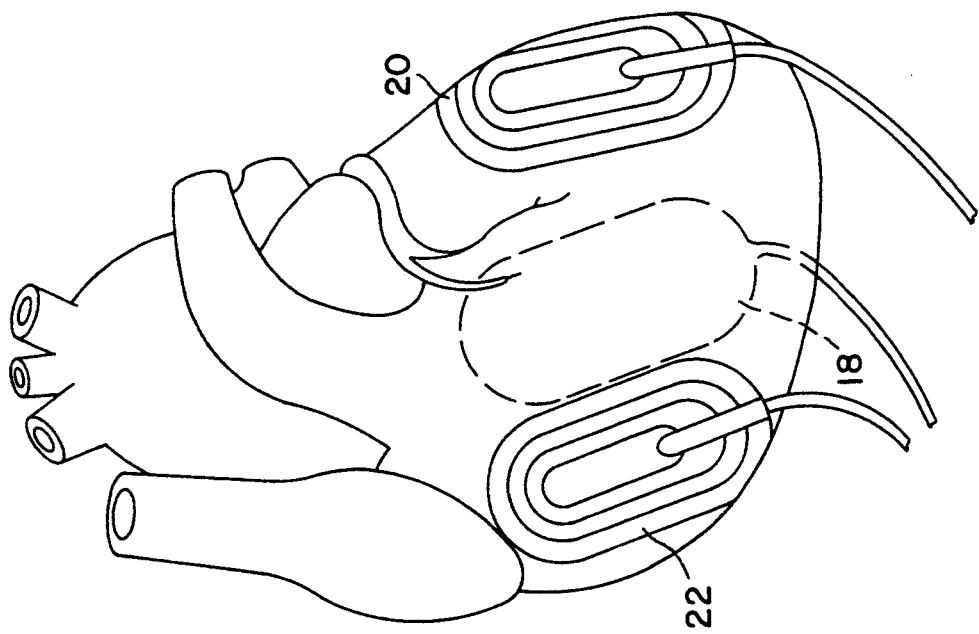
FIG. 3 is an illustration of a first electrode system for use in practicing the present invention.

FIG. 3 illustrates an electrode configuration for use in conjunction with the present invention. The system comprises three electrodes. One electrode 18, is located on the posterior right ventricle, one electrode 20, is located on the free left ventricular wall, and one electrode 22, is located on the anterior right ventricle. The first pulse may be applied between the anterior right ventricular electrode 22 and the left ventricular electrode 20 and the second pulse may be applied between the posterior right ventricular electrode 18 and the left ventricular electrode 20.

Figure 4:
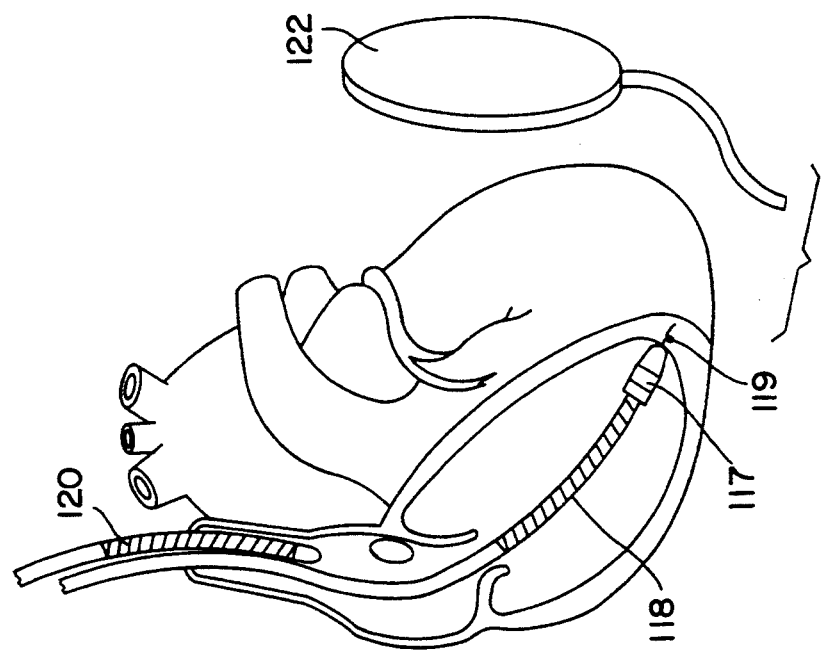
FIG. 4 is an illustration of a second electrode system for use in practicing the present invention.

FIG. 4 illustrates an alternative electrode configuration for use in conjunction with the present invention. The system comprises three electrodes. One electrode 118, is located in the right ventricle, one electrode 120, is located in the superior vena cava, and one electrode 122, is located subcutaneously in the left chest. The first pulse may be applied between electrode 118 and electrode 120 and the second pulse may be applied between electrode 118 and electrode 122. Helical electrode 119 and ring electrode 117 may be used to pace and sense the ventricle.

Figure 5:
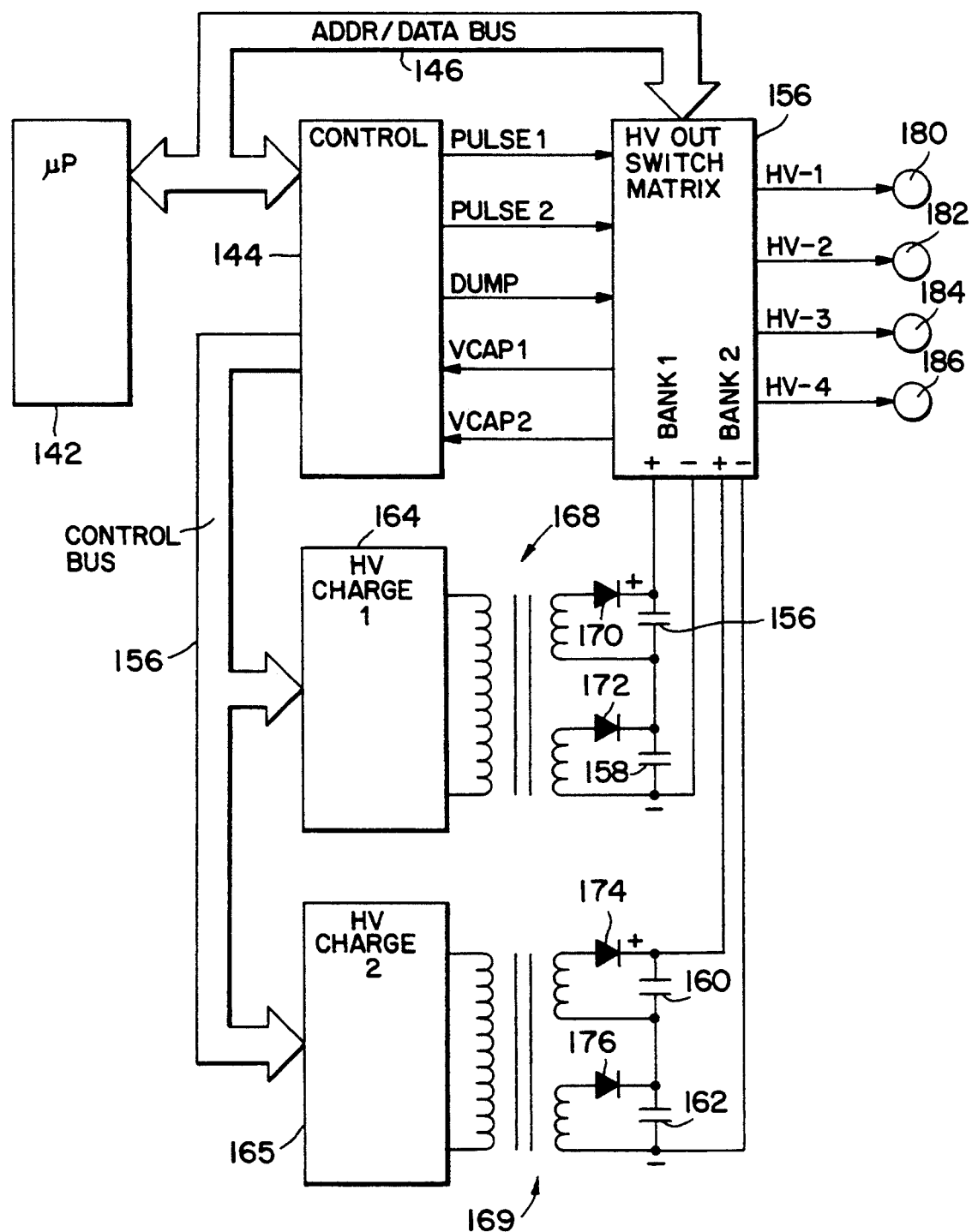
FIG. 5 is a block, functional diagram of a multiple pulse defibrillator of the type that could be employed to practice the present invention.

FIG. 5 illustrates a proposed embodiment of a multiple pulse defibrillator embodying present invention. All of the components illustrated are readily available and well known to the art, and therefore are illustrated in functional form only. FIG. 5 illustrates only those portions of the device associated with control of electrode selection and pulse duration and their interconnection to a microprocessor of the type typically employed to control the operations of pacemaker/cardioverter/defibrillators of the type in which the invention may usefully be employed. It should be understood that the illustrated circuitry will typically be coupled to the remainder of the device by means of the data/address bus 146, by which the microprocessor 142 also serves to control arrhythmia detection and cardiac pacing functions.

Output capacitors 156, 158, 160 and 102 form two capacitor banks. They are simultaneously charged by high voltage charging circuitry 164 and 165 by means of high voltage step-up transformers 168 and 169 controlled by control circuitry 144 via control bus 166. Charging is initiated in response to detection of a tachyarrhythmia by the microprocessor 142, as described in the above-cited Keimel patent. Diodes 170, 172, 174 and 176 rectify the AC signals provided by the transformers 168 and 169 to provide a net DC charge on the capacitors. The high voltage charging circuitry 164, 165 controlling the delivery of electrical current to the step-up transformers may correspond to that disclosed in U.S. Pat. No. 4,548,209, issued to Wielders et al, incorporated herein by reference in its entirety.

The voltage on the first capacitor bank 156, 158 is provided to control circuitry 144 on VCAP 1 line 154. The voltage on the second capacitor bank 160, 162 is provided to control circuitry 144 on VCAP 2 line 155. Charging continues until the voltages on lines 154 and 155 reach preset voltage thresholds defined by microprocessor 142. The voltage thresholds for the two capacitor banks will typically be the same, as the capacitor banks will be connected in parallel during the first pulse.

Four output electrodes are illustrated, including electrode 180, coupled to output line HV-1, electrode 182 coupled to output line HV-2, electrode 184 coupled to output line HV-3 and electrode 186 coupled to output line HV-4. However, as illustrated in FIGS. 3 and 4, the invention may usefully be practiced with three electrodes and the invention may correspondingly be practiced with more than four electrodes. Control of the timing of the pulses is provided by control circuitry 144, which sequentially provides high logic signals on PULSE 1 line 148 and PULSE 2 line 150, corresponding to the desired timing and durations of the first and second pulses. Selection of the electrodes employed to deliver the pulses, and of the polarity of the pulses is accomplished by microprocessor 142 via output switch matrix 156.

Control of the duration of the first and second pulses is preferably accomplished in response to the degree of discharge of the capacitor banks during the first pulse, as disclosed in the above-cited Winstrom and Bach et al patents. For example, the control logic 144 may respond to the voltage signals on the VCAP 1 and VCAP 2 lines and trigger termination of the first pulse in response to the voltage on the capacitor banks reaching a predetermined level, e.g. one half of their original voltage. In this case, the second pulse would have a leading edge voltage equal to the first pulse. Similarly, the second pulse could be terminated when the combined voltage of the two banks, in series, as indicated on the VCAP1 line reached a lesser value. Alternatively, the first and second pulses may simply be of fixed duration.

Interconnection of the capacitor banks and the electrodes is provided by means of a sets of electronic switches within switch matrix 156 which are selected by microprocessor 142 via address/data bus 146. During the first pulse, switches in matrix 156 couple the positive terminals of the first capacitor bank 156, 158 and the second capacitor bank 160, 162 to a selected electrode or electrodes and couple the negative terminals of the first and second capacitor banks to a different selected electrode or electrodes, in response to a high logic signal-on the PULSE 1 line. Switches in matrix 156 correspondingly couple the positive terminal of the first capacitor bank 156, 158 to a selected electrode or electrodes, couple the positive terminal of the second capacitor bank 160, 162 to the negative terminal of the first capacitor bank and couple the negative terminal of the second capacitor bank to a different selected electrode or electrodes during the second pulse, in response to a high logic signal on the PULSE 2 line.

The electrodes used for the first and second pulses may be entirely separate from one another, for example employing electrodes 180 and 182 during the first pulse and employing electrodes 184 and 186 during the second pulse. Alternatively an electrode or electrodes may be used as a common electrodes during both pulses, as would be the case using electrode systems as illustrated in FIGS. 3 and 4.

In response to a high logic signal on the DUMP line, matrix 156 couples the positive terminals of both capacitor banks to ground, to provide for internal discharge of the capacitor banks if therapy is aborted. Between pulses and during charging, (when the logic lines to the switch matrix as illustrated are all low) the switch matrix 156 couples the negative terminals of both capacitor banks to ground.

The switches in matrix 156 employed to couple the positive terminals of the capacitor banks to the electrodes may correspond to the trial switches disclosed in the above-cited Keimel patent, which may correspondingly be used to connect to the positive terminals of the capacitor banks therein to selected electrodes. Alternatively, FET switches as disclosed in the above-cited Winstrom et al patent may be employed if overall energy level demands are sufficiently low. SCR switches as described in the above-cited Mehra, et al., and Bach, et al., patents might also be employed. The electronic switches employed to couple the negative terminals of the capacitor banks to the electrodes and to couple the capacitor banks to one another in series may be, for example, FET switches as described in the above-cited Winstrom, et al., patent or SCR switches as described in the above-cited Mehra, et al., and Bach Jr., patents.

The circuitry illustrated in FIG. 5 may be readily incorporated into an implantable pacemaker/cardioverter/defibrillator, particularly a device similar to those currently in clinical evaluation by Medtronic, Inc. Alternatively, the device may similarly be practiced in the context of implantable pacemaker/cardioverter/defibrillators as disclosed in U.S. Pat. No. 4,791,058, issued to Pless et al., U.S. Pat. No. 4,380,006, issued to Haluska et al., or U.S. Pat. No. 5,063,928, issued to Grevis et al., all of which are incorporated herein by reference in their entireties.

While the disclosed embodiment is illustrated in a form adapted for inclusion in a microprocessor based implantable pacemaker/cardioverter/defibrillator, the invention may also usefully be practiced in defibrillators and cardioverters employing other circuit architecture including full custom digital logic or circuitry constructed of discreet, commercially available analog and digital components, so long as the essential functions and operations are preserved. As such, the above disclosure should be considered exemplary, rather than limiting with regard to the claims that follows.

In conjunction with the above specification, I claim:

1. Apparatus for cardiac cardioversion or defibrillation, comprising:
    a first pair of cardioversion or defibrillation electrodes;
    a second pair of cardioversion or defibrillation electrodes;
    a first capacitor having positive and negative terminals;
    a second capacitor having positive and negative terminals;
    means for coupling for said positive and negative terminals of said first and second capacitors, in parallel, to said first electrode pair to discharge said first and second capacitors for a first time interval to deliver a first cardioversion or defibrillation pulse and for subsequently coupling said positive terminal of said second capacitor to said negative terminal of said first capacitor and coupling said positive terminal of said first capacitor and said negative terminal of said second capacitor to said second electrode pair for a second time interval to further discharge said first and second capacitors to deliver a second cardioversion or defibrillation pulse.

2. Apparatus according to claim 1 wherein said first and second electrode pairs comprise a total of three electrodes and wherein one of said three electrodes comprises a common electrode, common to both said first and second electrode pairs.

3. Apparatus according to claim 1 or claim 2 wherein said coupling means comprises means for controlling durations of said first and second time intervals.

4. Apparatus according to claim 3 wherein said coupling means comprises means for controlling duration of said first time interval as a function of degree of discharge of said first and second capacitors.

5. A method of cardiac cardioversion or defibrillation of a patient's heart, comprising:
    applying a first pair of cardioversion or defibrillation electrodes to said patient;
    applying a second pair of cardioversion or defibrillation electrodes to said patient;
    coupling positive and negative terminals of first and second capacitors in parallel to said first electrode pair to discharge said first and second capacitors for a first time interval to deliver a first cardioversion or defibrillation pulse and subsequently coupling said positive terminal of said second capacitor to said negative terminal of said first capacitor and coupling said positive terminal of said first capacitor and said negative terminal of said second capacitor to said second electrode pair for a second time interval to further discharge said first and second capacitors to deliver a second cardioversion or defibrillation pulse.

6. A method according to claim 5 wherein said step of applying said first and second electrode pairs comprises applying a total of three electrodes, such that one of said three electrodes comprises a common electrode, common to both said first and second electrode pairs.

7. A method according to claim 5 or claim 6 wherein said coupling step comprises the step of controlling duration of said first time interval as a function of degree of discharge of said first and second capacitors.

8. Apparatus for cardiac cardioversion or defibrillation, comprising:
    a first pair of cardioversion or defibrillation electrodes;
    a second pair of cardioversion or defibrillation electrodes;
    capacitor means for storing electrical energy, comprising first and second capacitors;
    means for coupling said first and second capacitors in parallel to said first electrode pair to discharge said first and second capacitors for a first time interval to deliver a first cardioversion or defibrillation pulse and for subsequently coupling said first and second capacitors in series to said second electrode pair for a second time interval to further discharge said first and second capacitors to deliver a second cardioversion or defibrillation pulse; wherein said coupling means comprises means for controlling duration of said first time interval as a function of degree of discharge of said capacitor means.

9. Apparatus according to claim 8 wherein said coupling means comprises means for controlling duration of said second time interval as a function of degree of discharge of said capacitor means.

* * * * *